United States Patent [19]

Stolarczyk

[11] 4,105,523

[45] Aug. 8, 1978

[54] BIOCHEMICAL OXYGEN DEMAND MEASURING DEVICE

[75] Inventor: Larry G. Stolarczyk, Raton, N. Mex.

[73] Assignee: A. R. F. Products, Inc., Raton, N. Mex.

[21] Appl. No.: 672,514

[22] Filed: Mar. 31, 1976

[51] Int. Cl.² .......................................... G01N 27/46
[52] U.S. Cl. .............................. 204/195 B; 204/1 T; 204/129; 204/231
[58] Field of Search ................... 204/1 T, 1 Y, 195 B, 204/129

[56] References Cited

U.S. PATENT DOCUMENTS

| | | | |
|---|---|---|---|
| 3,045,665 | 7/1962 | Moyat | 204/129 |
| 3,162,585 | 12/1964 | DeFord et al. | 204/1 T |
| 3,282,803 | 11/1966 | Poepel et al. | 204/1 Y |
| 3,380,905 | 4/1968 | Clark | 204/195 P |
| 3,403,090 | 9/1968 | Tajiri et al. | 204/195 S |
| 3,668,102 | 6/1972 | Young | 204/195 B |
| 3,772,176 | 11/1973 | Pippen et al. | 204/1 Y |

Primary Examiner—T. Tung
Attorney, Agent, or Firm—Burmeister, York, Palmatier, Hamby & Jones

[57] ABSTRACT

A biochemical oxygen demand measuring device which utilizes the decrease in pressure in an air space above the sample under measurement in a sealed reaction vessel to actuate an oxygen generator which utilizes an electrolysis cell communicating with the reaction vessel. The quantity of oxygen supplied by the oxygen generator is a measurement of the biochemical oxygen demand and is proportional to the quantity of electricity used in the electrolysis cell. Electrical pulses in a chain of constant amplitude and constant duration are applied to the electrolysis cell and the chain of pulses is interrupted by means responsive to the pressure in the reaction vessel to maintain the pressure in the reaction vessel constant. A counter is employed to count the pulses over a period of time as a measurement of the oxygen taken up by the reaction in the pressure vessel. A barometric correction device is employed with a sensing electrode in the electrolysis cell to control the pulses of electrical energy.

7 Claims, 3 Drawing Figures

BIOCHEMICAL OXYGEN DEMAND MEASURING DEVICE

The present invention relates to biochemical oxygen demand measuring devices and in particular to such devices for continuously measuring the oxygen which is chemically or biologically removed from a sample during a period of time.

Doctor John W. Clark developed a method for continuously determining oxygen uptake of a large and inhomogenous biological sample, and his work is described in the New Mexico State University, *Engineering Experimental Station Bulletin*, No. 11 (1959). Doctor Clark applied his technique to the automatic determination of biochemical oxygen demand of polluted water. An improved apparatus for measuring biochemical oxygen demand is described by James C. Young, William Garner and John W. Clark in *Analytical Chemistry*, Vol. 37, Pg. 784, May 1965. The Clark method maintains the pressure in a closed sample containing vessel constant by replenishing metabolically utilized oxygen by adding oxygen to the closed vessel. Oxygen supplied to the vessel is generated by electrolysis of a dilute acid by providing a constant current to the electrolysis cell, and the amount of oxygen added to the closed vessel is determined by calculating the "on" time of the electrolysis current. An improvement in this process is described in United States Pat. No. 3,668,102 of James C. Young entitled IMPROVEMENTS IN SYSTEM FOR MEASURING BOD BY ELECTROLYSIS granted June, 1972. The Young and Clark measuring devices utilized a clock mechanism to measure the "on" time for the electrolysis unit, and Pat. No. 3,772,176 to Pippen and Kremer entitled BIOCHEMICAL OXYGEN DEMANDS SYSTEM measured the period of "on " time by means of a time pulse generator and a pulse counter.

It is one of the objects of the present invention to provide a more accurate measurement of the quantity of oxygen supplied to the closed sample vessel. In the apparatus of the prior art, errors have occurred in the measurement of the amount of oxygen provided to the closed vessel. Even though a constant current is provided to the electrolytic cell for generating oxygen, the current has a rise time and a delay time which introduces an error in the measurement. Further, the electrolysis cell has two separate chambers, one of which is in communication with the atmosphere, and the level of the electrolyte in that chamber is utilized to determine oxygen requirements. Accordingly, the accuracy of the measurement is affected by changes in atmospheric pressure.

A further object of the present invention is to provide an apparatus for measuring biological oxygen demand which facilitates automated data recording. A clock measurement, such as disclosed in the Young Pat. No. 3,668,102 is not readily adapted to digital calculations, or display.

In accordance with the present invention, an apparatus is provided for measuring biochemical oxygen demand of a sample in which the sample is placed within a closed vessel of larger volume than the sample in order to provide an air space within the vessel above the sample. Microorganisms in the sample reduce organics therein and thereby consume oxygen. As a result, oxygen in the air space above the sample is removed to reduce the pressure within the vessel. A means is provided for detecting changes in pressure within the air space of the vessel with respect to the normal or threshold pressure, which in the example to follow is atmospheric pressure. The detecting means has an electrical switch, and the conductivity of the switch changes in response to a change in the pressure within the vessel through the threshold pressure. Actuation of the switch is utilized to control an oxygen source which communicates with the air space in the vessel and includes an electrolysis cell with a positive and a negative electrode. The switch is used to activate a source of pulses of electrical energy which has a pair of output terminals electrically connected to the positive and negative electrodes. The pulse energy source produces electrical pulses on the output terminals thereof of a single polarity at a constant frequency, each of the pulses containing the same quantity of electricity. As a result, each pulse of the electrical energy source causes the oxygen source to produce a given and fixed quantity of oxygen. Since the oxygen increases the pressure within the vessel, the switch will be actuated when the pressure passes through the threshold pressure, thereby deactivating the pulse source of electrical energy and the oxygen source. A counter is utilized to count the number of pulses of the energy source, thereby determining the total oxygen supplied to the sample during the period of the test.

The microorganisms in the sample also produce a reaction in the vessel in that $CO_2$ is released as a metabolic end product of the microorganism. The pressure in the vessel is further reduced by absorbing the carbon dioxide in potassium hydroxide (KOH) either in the form of a solution or in the form of pellets disposed within the air space of the vessel or in communication therewith.

The electrolysis cell of the present invention is constructed with two chambers, one of which contains the oxygen electrode and is in communication with the air space within the vessel, and the other of which contains the hydrogen electrode and is vented to the atmosphere. The first chamber of the electrolysis cell is sealed from the atmosphere, thus causing the electrolyte which communicates with both cells to have a surface level in the chamber vented to the atmosphere which varies in response to the pressure in the air space of the sample vessel. The level of the electrolyte in the vented chamber of the electrolysis cell is utilized to detect changes in pressure within the air space of the sample vessel. However, the level of the electrolyte in the vented chamber of the electrolysis cell is also responsive to changes in atmospheric pressure. In accordance with the present invention, contact to the electrolyte is provided through a plurality of separate electrodes positioned within the vented chamber of the electrolysis cell at different levels, and means is provided which is responsive to changes in atomspheric pressure for selecting which of the plurality of electrodes is utilized. The specific means constitutes a U tube open at one end and closed at the other end and containing mercury which partially fills the U tube. Accordingly, changes in atmospheric pressure detected through the open end of the U tube results in a change in the level of the mercury in the closed end of the U tube. Electrical contacts within the U tube are provided for each of the electrodes, and the mercury forms the terminal for the electrical switch.

The foregoing objects and advantages of the present invention will be more fully described in the following specification and the accompanying drawings illustrating the present invention, in which.

Figure 1:
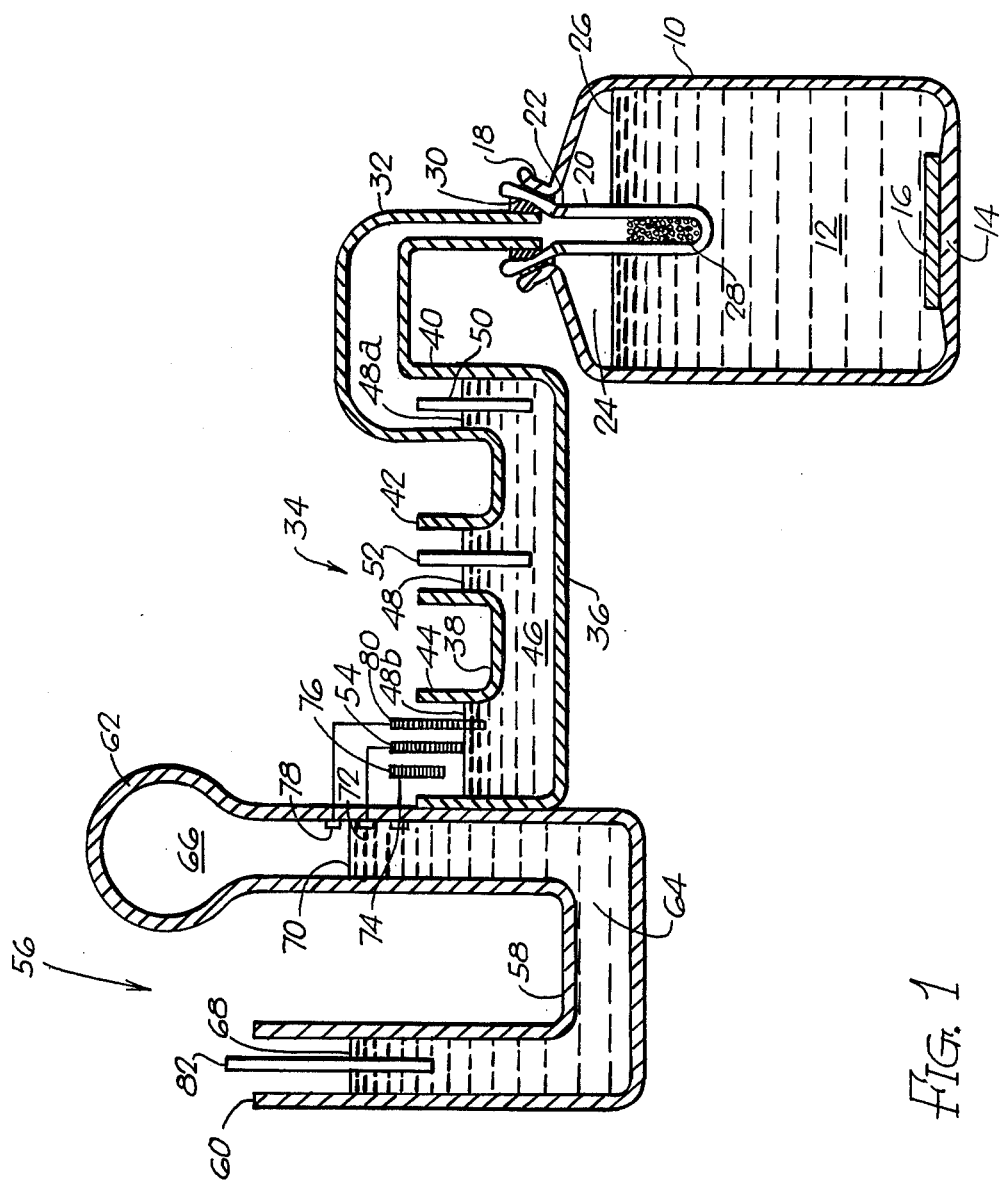
FIG. 1 is a sectional view of a reaction vessel, oxygen generator and barometric pressure correcting device constructed according to the teachings of the present invention.

FIG. 1 illustrates a vessel 10, sometimes referred to as a reaction chamber, which contains the sample 12 under measurement. As illustrated, the vessel is cylindrical and has a flat base 14 which supports a magnetic stirrer. The vessel 10 has an open neck 18 opposite the base 14, and an insert 20 is sealed within the opening and extends into the vessel 10. The vessel 10 and insert 20 are constructed of water impermeable materials, such as glass, and the insert is provided with a plurality of apertures 22 adjacent to the neck 18. The vessel is partially filled by the sample 12, and an air space 24 extends from the surface 26 of the sample 12 to the neck 18 of the vessel 10, and the apertures 22 in the insert 20 are disposed in the air space 24. The insert contains a plurality of pellets 28 of potassium hydroxide (KOH). The potassium hydroxide pellets are in communication with the air space 24 through the apertures 22 and absorb carbon dioxide ($CO_2$) which is released by reduction of the organic material in the sample 12 by action of the microorganisms therein. The insert 20 has an internal orifice 30 which is sealed on one end of an inverted U tube 32. The other end of the U tube 32 is sealed on an oxygen generator 34.

The oxygen generator 34 has a flat shallow vessel 36 which is provided with a cover 38. The cover 38 has a tubular protrusion 40 extending upwardly from one edge thereof and sealed on the end of the U tube 32 opposite the neck 18 of the reaction vessel 10. The vessel 36 also has a second circular protrusion 42 extending upwardly from the central portion of the vessel, and a third circular protrusion 44 extending upwardly from the side of the vessel 36 opposite the protrusion 40. The second and third tubular protrusions 42 and 44 are open to the atmosphere. The vessel 36 contains a body 46 of dilute acid, such as sulphuric acid which forms an electrolyte and rises to a level 48 well within the tubular protrusions 40, 42 and 44, as illustrated. A positive or oxygen electrode 50 is mounted within the tubular protrusion 40 and extends into the body 46 dilute acid, and a negative or hydrogen electrode 52 is mounted in the tubular protrusion 42 and extends into the body 46 of dilute acid. When a negative potential is placed upon the electrode 52 and a positive potential is placed upon the electrode 50, electrolysis of the body of hydrochloric acid results in the release of oxygen at the electrode 50 and hydrogen at the electrode 52. Since the tubular protrusion 40 is sealed into the air space 24 of the vessel 10, the oxygen liberated at the electrode 50 flows into the air space 24 to replace oxygen lost in the reaction vessel 10. Since the tubular protrusion 22 is open to the atmosphere, the hydrogen liberated at the electrode 52 escapes to the atmosphere.

Reduction of biological wastes within the sample 12 in the reaction vessel 10 result in a decrease in pressure in the air space 24, and accordingly, the level 48A of the body of dilute acid in the tubular protrusion 40 rises, thus causing the level of the dilute acid in the tubular protrusions 42 and 44 to fall. A sensing electrode 54 is mounted in the tubular protrusion 44 and extends just to the level 48B of the body of dilute acid within the protrusion 44 when the air space 24 is at its threshold pressure, which is normally atmospheric pressure. A decrease in pressure in the air space 24 of the reaction vessel 10 will result in the level 48B falling, thus breaking contact between the body 46 of dilute acid and the sensing electrode 54 and breaking the circuit through the body of dilute acid and the hydrogen electrode 52 from the sensing electrode 54.

Changes in the atmospheric pressure, or ambient pressure also affect the level 48B of the body 46 of dilute acid within the tubular protrusion 44, increases in pressure lowering the level 48B. Accordingly, a barometric pressure correcting device 56 is mounted on the vessel 36 adjacent to the tubular protrusion 44. The barometric pressure correcting device comprises an inverted U tube 58 open at one end 60 and provided with a substantially spherical closure 62 at the other end. A body of electrically conducting liquid 64, preferably mercury, is disposed within the U tube and traps a mass 66 of air within the spherical closure 62. The mass of air 66 acts as a spring, and compresses to equalize increases in pressure on the surface 60 of the body of mercury 64 in the open end 60 of the U tube 58, and expands to equalize reductions in pressure on the surface 68 in like manner, Accordingly, the level 70 of the mercury body in the closed leg of the U tube 58, adjacent to the closure 62, rises and falls in response to increases and decreases in atmospheric pressure, respectively. An electrically conducting contact 72 is mounted at the level 70 of the mercury body 64 when subjected to atmospheric pressure, and the contact 72 is electrically connected to the sensing electrode 54. A second contact 74 is mounted below the contact 72 in the closed leg of the U tube 58 and electrically connected to a second sensing electrode 76 which extends toward the level 48B in the tubular protrusion 44 a lesser distance than the sensing electrode 54 so that the sensing electrode 76 is out of contact with the body 46 of dilute acid when subjected to atmospheric pressure. A third electrical contact 78 is mounted within the closed leg of the U tube 58 above the contact 72 and electrically connected to a third sensing electrode 80 which extends further into the tubular protrusion 44 than the sensing electrode 54, thereby being immersed in the body 46 of dilute acid at atmospheric pressure. The barometric pressure correcting device 56 is provided with an output terminal in the form of an electrode 82 mounted in the open end 60 of the U tube 58 and extending into the body of mercury.

At atmospheric pressure and in the absence of a reaction in the vessel 10, the mercury in the closed leg of the U tube 58 rises to a level 70 which is aligned with a contact 72. At the same time, the level 48B in the tubular protrusion 48 rests at the level of the confronting end of the sensing electrode 54. Electrical contact is thus established through the output electrode 82, the electrically conducting mercury, the contact 72, the sensing electrode 54, the body of dilute sulphuric acid 46, and the hydrogen or negative electrode 52. If atmospheric pressure increases, the level 48A in the tubular protrusion 40 will rise, and the level 48B in the protrusion 44 will fall as a result. At the same time, the level 70 of the mercury body in the closed leg of the U tube 58 rises to immerse the contact 78. Accordingly, an electrical circuit is formed from the output electrode 82 through the body 64 of mercury, the contact 78, the sensing electrode 80, the body 46 of dilute sulphuric acid, and the hydrogen electrode 52. In like manner, if the atmospheric pressure falls, the level 48B in the tubular protrusion 44 rises to approach the sensing electrode 76. An electrical circuit may thus be established from the output electrode 82, through the body 64 of mercury, the contact 74, the sensing electrode 76, the body 46 of sulphuric acid, and the hydrogen electrode 52.

Figure 2:
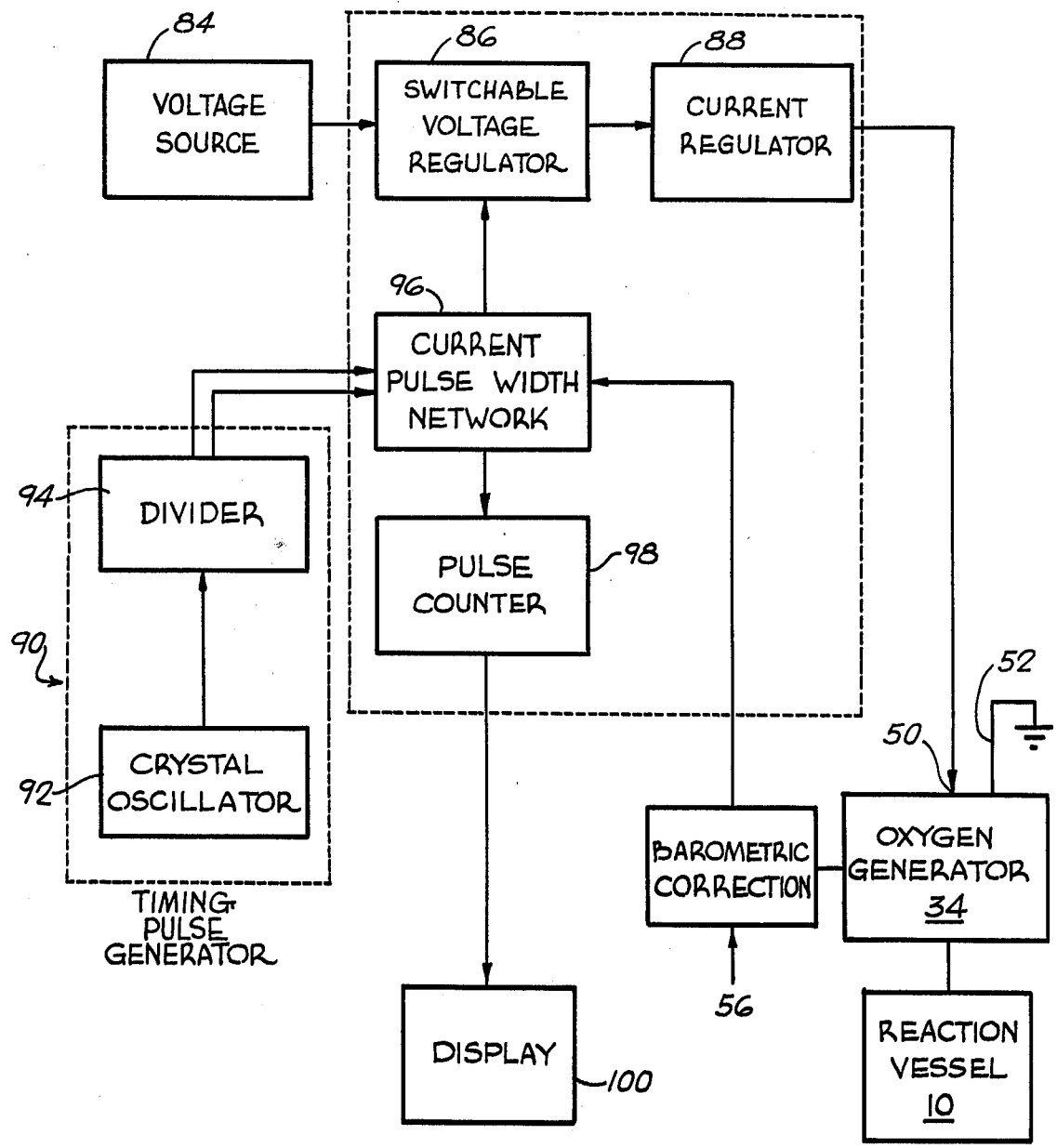
FIG. 2 is a block circuit diagram of a biochemical oxygen demand measuring device constructed according to the teachings of the present invention.

FIG. 2 illustrates the biochemical oxygen demand measuring device in block diagram. The reaction vessel 10, oxygen generator 34 and barometric device 56 have been described in detail with reference to FIG. 1. A voltage source 84, which may be a conventional direct current power source or a battery, is electrically connected to a switchable voltage regulator 86, and the output of the voltage regulator 86 is connected to a current reguator 88. The output of the current regulator is in the form of a chain of substantially square wave positive pulses of fixed duration, and is connected to the positive or oxygen electrode 50 of the oxygen generator 34.

A timing pulse generator 90 utilizing a crystal oscillator 92 in a frequency divider 94 is utilized to drive a current pulse width metwork 96. The current pulse width network controls the switchable voltage regulator 86 to produce the desired chain of pulses, and the current pulse width network 96 is controlled by the barometric correction device 56 so that the switchable voltage regulator 86 only produces pulses during the period in which oxygen is required in the reaction vessel 10.

The amount of oxygen by weight produced by the electrolysis of the dialectric is directly proportional to the quantity of electricity that passes through the dialectric in accordance with Faraday's Law. Accordingly, identical pulses of any wave form will each produce the same amount of oxygen if they contain the same quantity of electrical energy. Square wave pulses have been selected by the present inventor to be applied to the electrolysis cell because the amplitude of the current and the rise and fall times of such a pulse are readily controlled. A square wave pulse of ideal shape having an amplitude of 100 milliamperes per second and a duration of 12.05 seconds will produce 0.1 milligrams of oxygen. Hence the total number of milligrams of oxygen produced during the time period of the measured reaction may be obtained by merely counting the pulses. For this purpose, a pulse counter 98 is connected to the current pulse width network 96 and the output of the pulse counter 98 is shown on a display 100.

Figure 3:
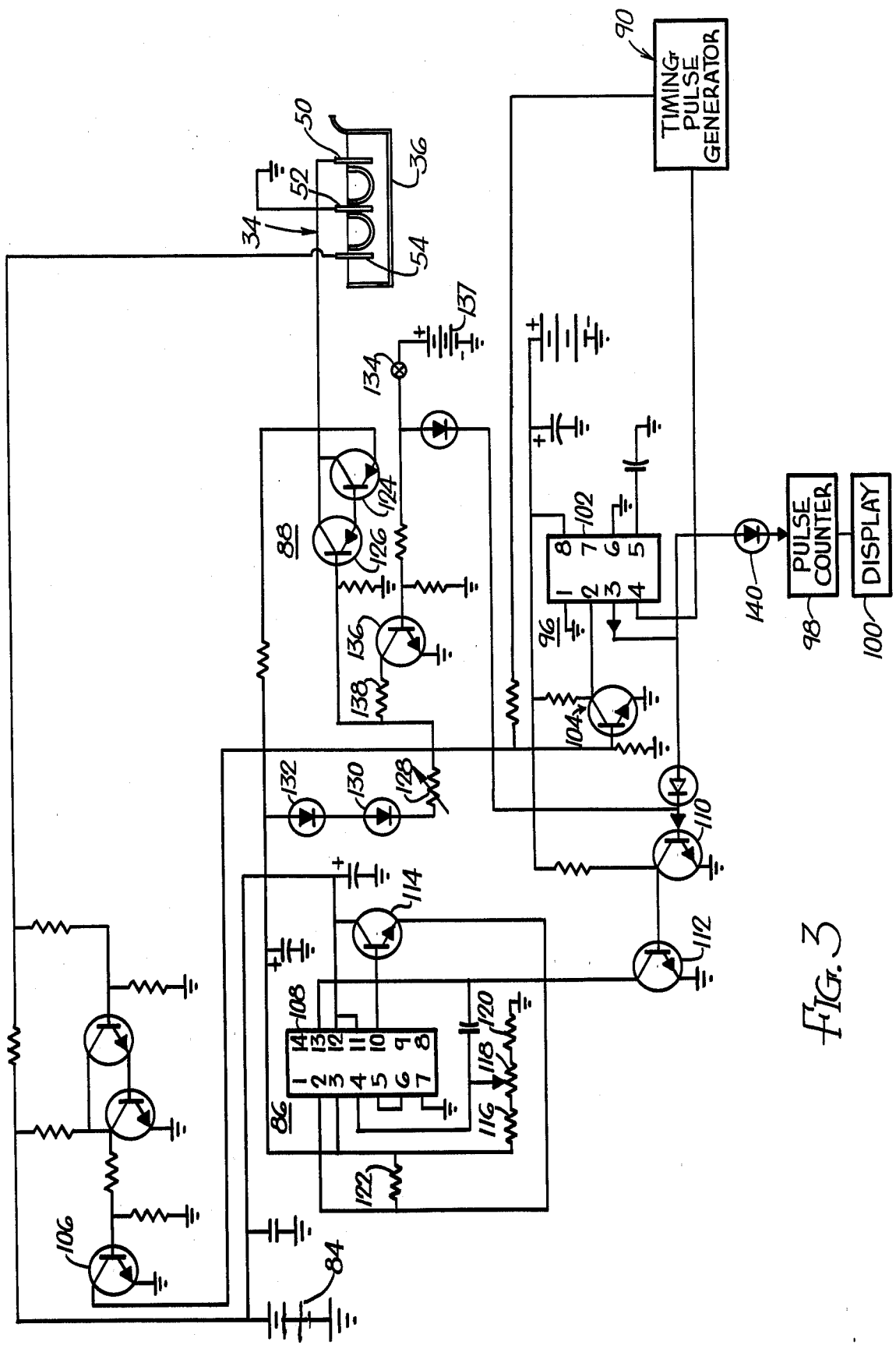
FIG. 3 is a schematic electric circuit diagram of the biochemical oxygen demand measuring device illustrated in FIG. 2.

The timing pulse generator 90 generates two isolated and synchronized chains of pulses, each pulse having a duration of 12.05 seconds and being separated by an approximately equal period. The two chains of pulses are used to control the current pulse width network 96 which is schematically illustrated in FIG. 3. The pulse width network 96 utilizes an integrated circuit 102 connected in a flip-flop circuit, and pin 4 of the integrated circuit 102 is connected to one of the outputs of the timing pulse generator 90 for the purpose of resetting the flip-flop when the pulse falls, and pin 2 of the integrated circuit 102 is coupled to the other output of the timing pulse generator 90 through a transistor switch 104 for the purpose of initiating the leading edge of the square wave pulse of the current pulse width network 96. The two outputs of the timing pulse generator 90 are identical in phase but isolated from each other.

The input to the base of the transistor switch 104 is controlled by the level of the dilute acid in the oxygen generator 34, which is diagrammatically shown in FIG. 3. For simplicity and clarity, the oxygen generator illustrated in FIG. 3 does not include the barometric pressure correcting device, and only one sensing electrode 54 is illustrated and is shown coupled to the base of a transistor 106 connected in a switching circuit, the emitter of the transistor 106 being grounded and the collector being connected to the base of the transistor of switch 104. Accordingly, during periods in which the sensing electrode 54 is in contact with the electrolyte, and grounded through the hydrogen electrode 52, the base of the switching transistor 104 is grounded through transistor 106, thus preventing the current pulse width network 96 from producing output pulses on pin 3 of the integrated circuit 102. However, when the level of the electrolyte falls below the sensing electrode 54, transistor 106 ceases to conduct, and the base of switching transistor 104 is driven by pulses from the timing pulse generator 90, thus producing a chain of pulses on pin 3 of the integrated circuit 102.

The output of the current pulse width network 96 appears on pin 3 of the integrated circuit 102 and is coupled to pin 13 of integrated circuit 108 of the switchable voltage regulator 86 through two transistors 110 and 112 connected in transistor switching circuits. Integrated circuit 108 controls the potential on the base of a voltage regulator transistor 114, the collector of the transistor 114 being connected to the positive terminal of the power source 84 and the emitter being connected to a voltage divider consisting of resistors 116, 118 and 120 through a small resistor 122. The output of the switchable voltage regulator 86 appears at the junction of resistors 116 and 118. When the collector to emitter voltage of transistor 112 is low, the output voltage of the switchable voltage regulator 86 is zero, and when the collector to emitter voltage of transistor 112 is high, the output voltage of the switchable voltage regulator 86 is at its regulated maximum value.

The output voltage appearing at the junction of resistors 116 and 122 is conducted to the current regulator 88. The current regulator 88 uses a transistor 124 with its emitter connected to the junction of transistors 116 and 122 of the switchable voltage regulator 86 and its collector connected to the oxygen electrode 50 for the purpose of controlling the magnitude of the current. A control transistor 126 has an emitter connected to the base of transistor 124 and a collector connected to the collector of transistor 124, and the base of transistor 126 is connected to the junction of resistors 116 and 122 through a variable resistor 128 and diodes 130 and 132. The potential on the base of transistor 126 controls the potential on the base of transistor 124 and the magnitude of current flowing through the electrolytic cell of the oxygen generator 34.

It is desirable to purge gases within the reaction vessel prior to initiating a measurement, and for this purpose, the current supplied to the electrolytic cell of the oxygen generator 34 is substantially increased. This is achieved by reducing the potential on the base of transistor 126 by means of a purge switch 134 connected between the base of a switching transistor 136 and the positive terminal of a power source 137, the switching transistor being connected to the base of transistor 136 through a resistor 138. In this manner, the oxygen generator 34 will produce a substantially larger volume of oxygen for the period of time in which the purge switch 134 is closed to facilitate initiation of the measurement.

The output of the current pulse width network 96, which appears upon pin 3 of integrated circuit 102, is conducted through a diode 140 to the pulse counter 98, and the count generated by the pulse counter 98 is conducted to the display 100. In this manner, the amount of oxygen supplied by the oxygen generator 34 during a period of time may be viewed directly on the display.

To measure the biochemical oxygen demand of a sample, a measured quantity of the sample, such as a liter, is placed within the vessel 10. The magnetic stirrer 60 at the bottom of the vessel 10 is actuated by a rotating magnet exterior of the vessel, not shown, in order to maintain the sample in uniformly mixed condition. Degradation of the organic material in the sample results in a decrease in the pressure in the air space 24, and actuation of the switch formed by contact of the sensing electrode 54 with the electrolyte, thus causing the switch formed by transistor 106 to open. Pulses from the timing pulse generator 90 are thus permitted to drive the current pulse width network 96 through transistor switch 104, and pulses from the current pulse width network 96 excite the switchable voltage regulator 86 to produce square regulator 86 to produce square wave pulses of uniform duration at the junction of resistors 116 and 122. These pulses are conducted through the current regulator 88 to the oxygen generator 34, and produce pulses of oxygen of identical weight, namely 0.1 milligrams per pulse in a preferred construction of the present invention. The pulses continue until the oxygen generated by the oxygen generator 34 restores the pressure in the air space 24 in the reaction vessel 10 and causes the electrolyte of the oxygen generator to regain contact with the sensing electrode 54. The pulse count during the lapse of time of the measurement is thus a precise measurement of the amount of oxygen by weight supplied to the air space 24, and a measurement of the oxygen consumed by the reaction in the reaction vessel 10.

Since the oxygen generated by each pulse of current flowing through the electrolyte is proportional to the quantity of electrical energy pulse, compensation can be made for differences in rise time and delay time of the pulses without affecting the accuracy of the measurement. A square wave pulse is produced by the apparatus of the preferred embodiment set forth above, but the positive portion of a sine wave or other wave form could also be utilized. The quantity of electrical energy in each pulse from the current regulator 88 is calibrated against a standard by adjustment of the variable resistor 128.

Those skilled in the art will devise many modifications and uses for the present invention over and above those here disclosed. It is therefore intended that the scope of the present invention be not limited by the foregoing specification, but rather only by the impending claims.

The invention claimed is:

1. Apparatus for measuring biochemical oxygen demand of a sample of a given volume comprising, in combination:
    a vessel having a volume substantially greater than the volume of the sample adapted to contain the sample thereby providing a space above the sample;
    an electrolysis cell having a first chamber and a second chamber and containing an electrolyte in the first and second chambers, said chambers communicating with each other at a level below the level of the electrolyte, said second chamber being closed and providing a closed space above the level of the electrolyte and the first chamber being open to the ambient atmosphere, the closed space of the second chamber being connected to and communicating with the space of said vessel;
    a sensing electrode extending in said first chamber to a predetermined level;
    a negative electrode immersed in said electrolyte in said first chamber at a level below said predetermined level;
    a positive electrode immersed in said electrolyte in said second chamber;
    a constant frequency pulse source of uniform duration and current having a positive output terminal electrically connected to the positive electrode and a negative output terminal electrically connected to the negative electrode;
    control means electrically connected to the pulse source for controlling the period of activation of the pulse source, said control means being electrically coupled to the sensing electrode and activating the pulse source during periods when the level of the electrolyte is below the sensing electrode and deactivating the pulse source during periods when the level of the electrolyte is in contact with the sensing electrode;
    and a counter responsive to electrical pulses electrically connected to the pulse source.

2. Apparatus for measuring biochemical oxygen demand of a sample of a given volume comprising, in combination:
    a vessel having a volume substantially greater than the volume of the sample adapted to contain the sample thereby providing a space above the sample;
    an electrolysis cell having a first chamber and a second chamber and containing an electrolyte in the first and second chambers, said chambers communicating with each other at a level below the level of the electrolyte, said second chamber being closed and providing a closed space above the level of the electrolyte and the first chamber being open to the ambient atmosphere, the closed space of the second chamber being connected to and communicating with the space of said vessel;
    a plurality of sensing electrodes extend into the first chamber of the electrolysis cell, each of the sensing electrodes extending to a different depth with respect to the level of the electrolyte in the cell;
    a negative electrode immersed in said electrolyte in said first chamber at a level below the level of the sensing electrodes;
    a positive electrode immersed in said electrolyte in said second chamber;
    a constant frequency pulse source of uniform duration and current having a positive output terminal electrically connected to the positive electrode and a negative output terminal electrically connected to the negative electrode;
    control means electrically connected to the pulse source for controlling the period of activation of the pulse source;

switching means for coupling the control means to one of the sensing electrodes, said switching means being responsive to an increase in ambient atmospheric pressure to switch the control means to a sensing electrode extending into the cell to a greater depth and responsive to a decrease in ambient atmospheric pressure to switch the control means to a sensing electrode extending into the cell to a lesser depth, said control means activating the pulse source during periods when the level of the electrolyte is below the one sensing electrode coupled to the control means and deactivating the pulse source during periods when the level of electrolyte is in contact with the one sensing electrode coupled to the control means;

and a counter responsive to electrical pulses electrically connected to the pulse source.

3. Apparatus for measuring biochemical oxygen demand of a sample of a given volume comprising, in combination;

a vessel having a volume substantially greater than the volume of the sample adapted to contain the sample thereby providing a space above the sample;

an electrolysis cell having a first chamber and a second chamber and containing an electrolyte in the first and second chambers, said chambers communicating with each other at a level below the level of the electrolyte, said second chamber being closed and providing a closed space and the first chamber being open to the ambient atmosphere, the closed space of the second chamber being connected to and communicating with the space of said vessel;

a sensing electrode extending in said first chamber to a predetermined level;

a negative electrode immersed in said electrolyte in said first chamber at a level below said predetermined level;

a positive electrode immersed in said electrolyte in said second chamber;

a constant frequency pulse source of uniform duration and current having a positive output terminal electrically connected to the positive electrode and a negative output terminal electrically connected to the negative electrode;

control means electrically connected to the pulse source for controlling the period of activation of the pulse source, said control means being electrically coupled to the sensing electrode and activating the pulse source during periods when the level of the electrolyte is below the sensing electrode and deactivating the pulse source during periods when the level of the electrolyte is in contact with the sensing electrode;

and a counter responsive to electrical pulses electrically connected to the pulse source;

wherein a plurality of sensing electrodes extend into the first chamber of the electrolysis cell, each of the sensing electrodes extending to a different depth with respect to the level of the electrolyte in the cell, in combination with a U tube constructed of electrically insulating material open at one end and closed at the other end, said U tube being partially filled with an electrically conducting liquid, a plurality of electrical contacts equal in number to the number of sensing electrodes in the electrolysis cell mounted in the U tube adjacent to the closed end thereof, each of said contacts being disposed at a different position along the axis of the U tube and being electrically connected to one of the sensing electrodes, the contact nearest the closed end of the U tube being electrically connected to the sensing electrode extending furthest into the electrolyte in the cell, and each of the contacts in order of distance from the closed end of the U tube being electrically connected to the sensing electrodes in the order of the depth to which the electrodes extend toward the electrolyte.

4. Apparatus for measuring biochemical oxygen demand comprising the combination of claim 1 wherein the constant frequency source of pulses produces square wave form, each pulse being of a current of approximately 100 milliampers per second and a duration of approximately 12.05 seconds.

5. Apparatus for measuring biochemical oxygen demand comprising the combination of claim 1 wherein the constant frequency of pulses comprises a flip-flop having a first control input terminal for initiating the rise of each pulse produced by the flip-flop and a second control input terminal for initiating the decay of each pulse produced by the flip-flop, and a timing pulse generator having a first output terminal connected to the first control input terminal of the flip-flop and a second output terminal connected to the second control input terminal of the flip-flop, said timing pulse generator producing a pulse train on the first and second output terminals thereof with transitions spaced as to time determining the pulse width of the flip-flop.

6. Apparatus for measuring biochemical oxygen demand comprising the combination of claim 5 wherein the control means for controlling the period of activation of the pulse source comprises a transistor switch having an emitter to collector circuit including the first control input terminal of the flip-flop, said transistor switch having one state in which the pulses of the timing pulse generator are isolated from the first control input terminal of the flip-flop, the base of the transistor switch being electrically coupled to the sensing electrode.

7. Apparatus for measuring biochemical oxygen demand comprising the combination of claim 5 wherein the constant frequency pulse source includes a switchable voltage regulator and a constant current regulator connected to cascade, the switchable voltage regulator being electrically coupled to the flip-flop.

* * * * *

UNITED STATES PATENT OFFICE
CERTIFICATE OF CORRECTION

Patent No. 4,105,523   Dated August 8, 1978

Inventor(s) Larry G. Stolarczyk

It is certified that error appears in the above-identified patent and that said Letters Patent are hereby corrected as shown below:

Col. 5, line 19, before "88", delete "reguator" and insert -- regulator --.

Col. 5, line 26, before "96", delete "metwork" and insert -- network --.

Col. 7, line 26, after "square" first occurrence, delete "regulator 86 to produce square".

Col. 10, line 57, Claim 7, after "connected", delete "to" and insert -- in --.

Signed and Sealed this

Thirteenth Day of February 1979

[SEAL]

Attest:

RUTH C. MASON
Attesting Officer

DONALD W. BANNER
Commissioner of Patents and Trademarks